US00PP18473P2

(12) United States Plant Patent
Carruth

(10) Patent No.: US PP18,473 P2
(45) Date of Patent: Feb. 5, 2008

(54) FLORIBUNDA ROSE PLANT NAMED 'WEKVOSSUTONO'

(50) Latin Name: *Rosa hybrida*
Varietal Denomination: WEKvossutono

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 11/523,832

(22) Filed: Sep. 19, 2006

(51) Int. Cl.
*A01H 5/00* (2006.01)

(52) U.S. Cl. ..... Plt./145

(58) Field of Classification Search ..... Plt./145
See application file for complete search history.

*Primary Examiner*—Kent Bell
(74) *Attorney, Agent, or Firm*—Christie, Parker & Hale, LLP

(57) ABSTRACT

A new variety of Floribunda rose suitable for garden decoration, having flowers of butter gold coloration.

1 Drawing Sheet

Classification: The present invention relates to a new *Rosa hybrida* plant.

Variety Denomination: The new plant has the varietal denomination 'WEKvossutono'.

BACKGROUND OF THE INVENTION

This invention relates to a new and distinct variety of Floribunda Rose. It has an undisseminated seedling of my creation as its seed parent with the following genetic origin {(Voodoo×*Rosa soulieana* derivative)×Summerwine}, and as its pollen parent the variety known as 'MACamster' (not patented).

SUMMARY OF THE INVENTION

Among the features which distinguish the new variety from other presently available and commercial rose cultivars known to the inventor are the following combination of characteristics: its entirely smooth peduncle, its strong licorice fragrance, its even butter good coloration that last throughout the life of the flower and its above average degree of resistance to black spot and powdery mildew. The plant has a compact and bushy growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKvossutono' may be asexually propagated by cuttings, budding and grafting. The budding and grafting successfully occurred on the plant/rootstock *Rosa hybrida* cv. 'Dr. Huey'.

Comparison with Parents

The new rose may be distinguished from its seed parent, an undisseminated seedling of my creation by the following combination of characteristics: whereas 'WEKvossutono' bears butter gold flowers of very double petalage (about 30 to 45 petals), the undisseminated seedling bears soft orange flowers with significantly lesser petalage (about 20 to 25 petals). The new variety bears glossy foliage, whereas the seed parent bears matte foliage.

The new variety may be distinguished from its pollen parent, 'MACamster' by the following combination of characteristics: whereas 'WEKvossutono' bears butter gold flowers with a strong licorice fragrance, 'MACamster' bears amber gold flowers with a moderate fruity fragrance. The new variety has a compact and bushy medium height mature growing habit (about 70 to about 85 cm. in height), whereas the pollen parent has an upright significantly taller mature growing habit (about 110 to about 130 cm. in height).

Comparison with the Closest Commercially Available Cultivar

The new variety may be distinguished from its closest commercially available cultivar, 'JACjem' by the following combination of characteristics: whereas 'WEKvossutono' bears flowers of very double petalage (about 30 to 45 petals) with strong licorice fragrance, 'JACjem' bears flowers with significantly lesser petalage (about 20 to 25 petals) with a slight fragrance. The new variety has a compact and bushy medium height mature growing habit (about 70 to 85 cm. in height), whereas 'JACjem' has a compact and significantly taller mature growing habit (about 90 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of August. Phenotypic expression may vary with environmental, cultural and climatic conditions, as well as differences in conditions of light and soil.

FLOWER

The new variety sometimes bears its flowers singly, usually in clusters of two to seven or more per stem. Flowers may be borne in regular rounded clusters on strong moderately short to medium length stems (about 18 to about 44 cm.). Outdoors, the plant blooms abundantly and nearly continuously during the growing season. The flowers have strong licorice fragrance.

BUD

The peduncle is about 2.7 to about 3.8 cm. in length, of average caliper (about 0.2 to about 0.3 cm. in diameter), and usually erect. It is entirely smooth. Peduncle color is between 145A and 146B sometimes lightly suffused, especially on the side exposed to the sun, with between 187C and 183C.

Before the calyx breaks, the bud is about 1.2 to about 1.7 cm. in diameter at the widest point, about 1.3 to about 1.8 cm. in length, and moderately ovoid to somewhat pointed in shape with a conspicuous neck. The surface of the bud bears few foliaceous appendages and some hairs, usually with slender entire foliaceous parts extending beyond the tip of the bud about ¼ or more of its length. Bud color is between 144A and 138B sometimes lightly suffused, especially on the side exposed to the sun, with between 187C and 183C.

The sepals are about 1.9 to about 2.7 cm. in length and about 0.8 to about 1.1 cm. in width at the widest point. The outer surface color of the sepal is between 144A and 138B sometimes lightly suffused, especially on the side exposed to the sun, with between 187C and 183C. The inner surface color of the sepal is between 146C and 137B and covered with fine wooly tomentum; sepal margins are sometimes lined with very few stipitate glands and numerous hairs.

The receptacle of the flower is of medium length (about 0.5 to about 0.8 cm.) and moderately heavy in caliper (about 0.8 to about 1.1 cm. in diameter). The receptacle is moderately ovoid to somewhat globular in form. Its surface is very smooth with thick fleshy walls. The receptacle color is between 144A and 138B.

As the petals open (after the calyx breaks), the bud is about 1.8 to about 2.2 cm. in diameter at the widest point, about 2.0 to about 2.6 cm. in length, and moderately ovoid to somewhat globular in form. The color at the base of the under surfaces of the newly opened petals is between 12A and 13B gradually suffusing toward the edge of the petals with between 24B and 21B. The color at the base of the upper surfaces of the newly opened petals is near 14B gradually suffusing toward the edge of the petals with between 23A and 21B.

BLOOM

When fully open, the bloom ranges from about 5.7 to about 11.4 cm. in diameter. Petalage is very double with about 30 to 45 petals and about 5 to 9 petaloids irregularly arranged. When partially open, the bloom form is moderately globular to cupped, and the petals are somewhat loosely spiraled to undulated with petal edges slightly reflexed outward and inward. When fully open, the bloom form is cupped and the petals are loosely cupped to undulated with petal edges moderately reflexed outward and inward.

PETALS

The substance of the petals is moderately heavy and of medium thickness, with upper surfaces slightly satiny and under surfaces matte to slightly shiny. The petals are about 2.2 to about 4.1 cm. in length and about 1.2 to about 3.9 cm. in width at the widest point. Petal margins are entire.

The outer petals are moderately obovate to somewhat rounded in shape with rounded apices to sometimes somewhat mucronate.

The inner petals are obovate to somewhat oblanceolate in shape with rounded apices to sometimes somewhat mucronate.

Petaloids are about 1.2 to about 2.7 cm. in length and about 0.6 to about 1.7 cm. in width at the widest point. Petaloids are irregularly shaped somewhat obovate to oblanceolate with rounded apices.

NEWLY OPENED FLOWER

On the under surfaces of the outer, intermediate and inner petals, the color at the base of the petals is near 12B, gradually suffusing toward the edge of the petals with between 16B and 16C. There is no visible change in coloration at the point where the petal attaches on the under surface. On the upper surfaces of the outer, intermediate and inner petals, the color at the base of the petals is between 12A and 12B, gradually suffusing toward the edge of the petals with between 13B and 17D. There is no visible change in coloration at the point where the petal attaches on the upper surface.

The under and upper surface color of the petaloids are similar in coloration to the upper and under surfaces of the outer, intermediate and inner petals.

The general tonality of the new opened flower is between 13B and 17D.

THREE-DAY-OLD FLOWER

On the upper surfaces of the outer, intermediate and inner petals, the color at the base of the petals is between 10A and 8B, gradually suffusing toward the edge of the petals with between 16C and 11D. At the point where the petal attaches, there is a very small zone of between 9C and 8A. On the upper surfaces of the outer, intermediate and inner petals, the color at the base of the petals is between 9C and 10A, gradually suffusing toward the edge of the petals with between 14D and 11D. At the point where the petal attaches, there is a small zone of between 12A and 12B.

The under and upper surface color of the petaloids are similar in coloration to the upper and under surfaces of the outer, intermediate and inner petals.

The general tonality of the three-day-old flower is between 14D and 11D.

On the spent bloom, the petals usually drop off cleanly.

In August in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 160) and are arranged regularly about the pistils; a few are mixed with petaloids or tucked in the calyx. The filaments are of moderately long length (about 0.8 to about 1.3 cm.) most with anthers. Filaments are between 12A and 9A in color. The anthers are somewhat small for the class and all open approximately at the same time. Anther color is between 23B and 16D when immature and between 200B and 165D at maturity. Pollen is abundant and near 20B in color.

FEMALE REPRODUCTIVE ORGANS

Pistils vary in number (average about 92). The styles are moderately even, short in length (about 0.2 to about 0.5 cm), thin in caliper, and loosely bunched to separated. Stigma color is between 7D and 8B. Style color is between 1D and 150D usually lightly suffused with between 53C and 53D. Ovaries are all enclosed in the calyx.

Hips are of average length (about 1.0 to about 1.5 cm.), rounded in form, and between 24A and 28B in color when ripe. The hip surface is very smooth with thick fleshy walls. The sepals are permanent and usually straight in shape.

The seeds are irregularly rounded, smooth in texture, approximately 14 to about 20 per hip, about 0.3 to about 0.6 cm. in diameter at the widest point and between 161A and 162C in color.

FOLIAGE

The compound leaves are usually comprised of three to five leaflets and are borne abundantly. The five-leaflet leaves are about 9.0 to about 13.8 cm. in length and about 7.4 to about 10.6 cm. in width at the widest point, moderately leathery to somewhat crisp in texture, and glossy in finish. The terminal leaflets are about 4.4 to about 7.4 cm. in length and about 2.5 to about 4.8 cm. in width at the widest point, shaped ovate to moderately oval with acute apices and rounded bases. Their margins are simply serrate.

The upper surface color of the mature leaf is between 147A and 139A. The under surface color of the mature leaf is between 147B and 139C. The upper surface color of the young leaf is between 146 and 146B, usually lightly suffused with between 183A and 187A. The under surface color of the young leaf is between 146B and 146C, usually lightly suffused with between 183A and 187B.

The rachis is moderately light in caliper and moderately rough. The upper side is shallowly grooved with some hairs and few stipitate glands on the edges of the grooves. The under side of the rachis is moderately rough with few small prickles. The rachis color is between 145A and 146B, usually lightly suffused on the young leaves with between 183A and 187B.

The stipules are about 1.1 to about 1.6 cm. in length and of medium width (about 0.4 to about 0.6 cm.) with medium length straight points that usually turn out at an angle of more than 45 degrees and often recurve toward the stem. The stipules color is between 145A and 146B.

The petiole is moderately light in caliper and moderately rough. The upper side is shallowly grooved with some hairs and few stipitate glands on the edges of the grooves. The under side of the petiole is moderately rough with few small prickles. The petiole is about 0.7 to about 3.0 cm. in length and about 0.1 to about 0.2 cm in diameter at the widest point. The petiole color is between 145A and 146B, usually lightly suffused on the young leaves with between 183A and 187B.

The plant displays an above average degree of resistance to powdery mildew, downy mildew, black spot and rust as compared to other commercial varieties grown under comparable conditions in Upland, Calif. The plant's winter hardiness and drought/heat tolerance are yet to be determined.

GROWTH

The plant has a compact and bushy medium height growing habit (about 70 to about 85 cm. in height and about 50 to about 65 cm. spread at the widest point), with very full branching. It displays moderately vigorous growth and the canes are somewhat heavy in caliper for the class.

The color of the major stems is between 152A and 148A. They bear many large prickles that are about 0.6 to about 1.0 cm. in length. The large prickles are moderately angled to slightly hooked downward with a somewhat short length narrow oval base; prickle color is between 165B and 199C. The major stem bears few small prickles of similar shape and coloration.

The color of the branches is between 146B and 138B. They bear many large prickles which are of similar shape to the large prickles on the major stems. Prickles are about 0.4 to about 0.6 cm. in length. The color is between 165B and 166C. The branches bear few small prickles of similar shape and coloration.

The color of the new shoots is between 144A and 138B sometimes lightly suffused, especially on the side exposed to the sun, with between 187C and 183C. They bear some large prickles which are of similar size and shape to the large prickles on the branches; prickle color is between 151B and 150B sometimes moderately suffused with between 187D and 183D. The shoots bear very few small prickles of similar shape and coloration.

What is claimed is:

1. A new and distinct Floribunda rose plant of the variety substantially as described and illustrated herein.

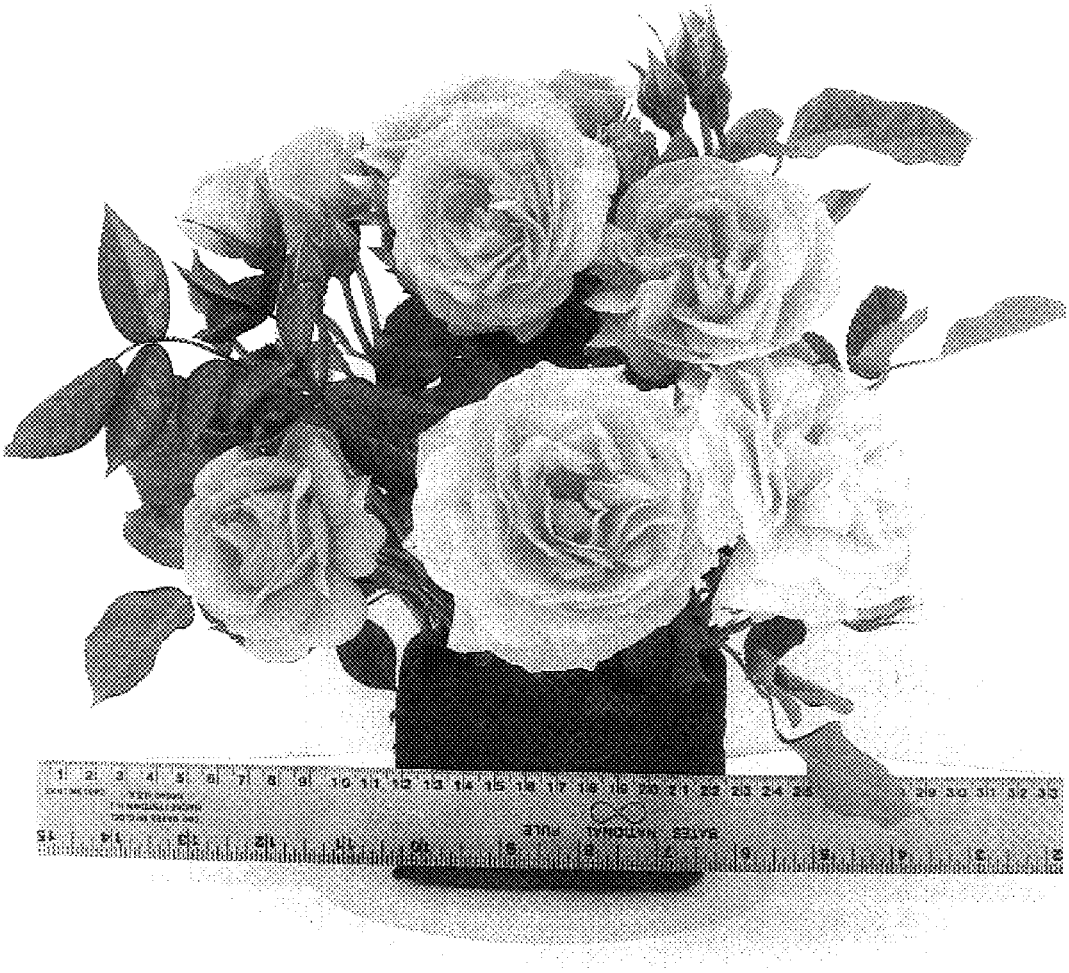

* * * * *